United States Patent

Smith

(10) Patent No.: US 8,599,032 B2
(45) Date of Patent: Dec. 3, 2013

(54) SYSTEM AND METHOD FOR DETECTION OF OVERSIZE PARTICLES IN THE UNDERFLOW OF A VIBRATORY SEPARATOR

(75) Inventor: Joseph L. Smith, Cincinnati, OH (US)

(73) Assignee: M-I L.L.C., Houston, TX (US)

( * ) Notice: Subject to any disclaimer, the term of this patent is extended or adjusted under 35 U.S.C. 154(b) by 491 days.

(21) Appl. No.: 12/934,740

(22) PCT Filed: Mar. 26, 2009

(86) PCT No.: PCT/US2009/038355
§ 371 (c)(1),
(2), (4) Date: Sep. 27, 2010

(87) PCT Pub. No.: WO2009/120835
PCT Pub. Date: Oct. 1, 2009

(65) Prior Publication Data
US 2011/0012733 A1    Jan. 20, 2011

Related U.S. Application Data

(60) Provisional application No. 61/040,004, filed on Mar. 27, 2008.

(51) Int. Cl.
*G08B 21/00* (2006.01)
(52) U.S. Cl.
USPC ............ 340/679; 209/549; 209/552; 340/657
(58) Field of Classification Search
USPC ............... 340/679, 657, 663, 636.1, 636.15; 209/233, 320, 325, 331, 346, 546, 548, 209/549, 552, 920
See application file for complete search history.

(56) References Cited

U.S. PATENT DOCUMENTS 7,093,718 B2 *    8/2006  Kato et al. ............... 209/262

FOREIGN PATENT DOCUMENTS

| JP | 62-024980 U | 2/1987 |
|----|----|----|
| JP | 3492676 B2 | 2/2004 |

OTHER PUBLICATIONS

Examiner's Report issued in corresponding Canadian Application No. 2,719,622; Dated Jan. 5, 2012 (2 pages).
International Search Report issued in PCT/US2009/038355, mailed on Nov. 10, 2009, 3 pages.
Written Opinion issued in PCT/US2009/038355, mailed on Nov. 10, 2009, 4 pages.

* cited by examiner

*Primary Examiner* — Thomas Mullen
(74) *Attorney, Agent, or Firm* — Osha Liang LLP

(57) ABSTRACT

System and method for detection of oversize particles in the underflow of a vibratory separator and method for measuring the operability of a vibratory separator. The system comprises a sampling line connected to the underflow discharge line of the vibratory separator for sampling a portion of material, a centrifugal sensing pump powered by an electric motor with a power supply measuring device, a sampling screen, and a return line. A reduction in power supplied to the electric motor indicates a reduction in flow of material through the sampling screen as a result of oversize particles in the underflow of the vibratory separator. A baseline amount of power supplied to the electric motor may be measured and recorded. The subsequent amount of power supplied to the electric motor may then be compared to the recorded baseline amount to measure the operability of the vibratory separator.

20 Claims, 6 Drawing Sheets

SYSTEM AND METHOD FOR DETECTION OF OVERSIZE PARTICLES IN THE UNDERFLOW OF A VIBRATORY SEPARATOR

BACKGROUND

1. Field of the Disclosure

Embodiments disclosed herein relate generally to separators, and more particularly to separators for screening materials using vibratory motion for enhanced screening, and even more particularly to systems and methods for the detection of oversize particles in the underflow of a vibratory separator.

2. Background Art

Vibratory separators have long been used for the separation of both dry and wet materials, and are used in industries as varied as the chemical, food and beverage, powder coating, pharmaceutical, plastic, pulp and paper, ceramic, oilfield, and laundry industries. Such separators may be circular or rectangular in cross section, and they generally include a vibration generating device and resiliently mounted housings. Screens are fixed to the vibratory housings such that material fed to the vibrating screens may be screened. Various vibratory motions may be employed to work the material on the screen in the most advantageous manner. Frequently, discharge openings are provided both above the screening mechanism and below for retrieving the separated materials.

Some factors for selecting a particular vibratory separator include general material information, material characteristics, wet material data, MSDS information, separator efficiency requirements, and desired use for the vibratory separator. For example, general material information may include the material to be screened, the temperature of the material, bulk density, specific gravity, and particle shape (spherical, fibrous, platelet, etc.). Materials may be characterized as granular, powder, abrasive, electrostatic, sticky, corrosive, free flowing, and agglomerates, among other characterizations. Key wet material data may include whether the material is viscous, greasy/oily, thixotropic, paste-like, sticky, or fatty. Furthermore, standard process data such as feed rate and minimum/maximum percentage of solids are important factors for selection of a vibratory separator. MSDS information, including numbers representing the severity of health, flammability and reactivity may be important depending on industry and application. Efficiency requirements vary by industry and application and are also important factors. Finally, those of ordinary skill in the art will appreciate that a vibratory separator may be used to scalp, dedust, or dewater, among other alternative uses.

In operation, a vibratory separator may be actuated to provide a flow of materials through the vibratory separator, such that solid particles are divided according to relative size. Thus, as the materials flow over a screen, larger particles exit the vibratory separator through a discharge, while smaller particles exit through a secondary discharge area. The screen may include a plurality of filtering elements that may be manufactured from metals, plastics, cloth, and/or composites. Screens may be selected based on mesh size or micron size, among other sizing selection alternatives. Those of ordinary skill in the art will appreciate that multiple screens may be used, with each screen having its own screen size, allowing for a plurality of discharges, each with its own allowable "overs" percentage and allowable "unders" percentage.

Over time, screens may be exposed to erosive and/or corrosive substances and operational conditions that degrade the screen effectiveness or efficiency of the filtering elements. Examples of operational conditions that may cause such an effect include typical actuation of the vibratory separator to impart movement in vertical and lateral directions. Over time, the vibratory motion, for example, in the vertical direction, may decrease the integrity of the screens due to structural damage, filtering element loosening, and the like. Such decreases in integrity may manifest as a slackening of the screen or parting of the screen from the frame, frame warpage or failure, or failure of the filtering element at the intersection with the frame. Further, screen failure may result from a broken screen, a screen tear, or bypass around a screen from improper sealing.

Screen failure may result in oversize particles entering the discharge underflow line of a vibratory separator. In wet screening of certain products, a maximum particle size may be important to manufacturing processes, and failure to screen to such a maximum size may lead to a large amount of final product being rejected or having to be reworked at a significant expense.

Accordingly, there exists a need for systems and methods for the detection of oversize particles in the underflow of a vibratory separator.

SUMMARY OF THE DISCLOSURE

In one aspect, embodiments disclosed herein relate to a system for detection of oversize particles in the underflow of a vibratory separator. The system includes a sampling line connected to the underflow discharge line of the vibratory separator for sampling a portion of material, a centrifugal sensing pump powered by an electric motor, a sampling screen, and a return line for returning the sampled portion of material. The system further includes a power supply measuring device operatively connected to the electric motor. A reduction in power supplied to the electric motor indicates a reduction in flow of material through the sampling screen.

In another aspect, embodiments disclosed herein relate to a method for detection of oversize particles in the underflow of a vibratory separator. A portion of material is sampled from the underflow discharge line of a vibratory separator. The portion of material flows to a centrifugal sensing pump powered by an electric motor, flows to a sampling screen, and returns to the main underflow discharge line. The method further includes measuring the power supplied to the electric motor. A reduction in power to the electric motor indicates a reduction in flow of material through the sampling screen as a result of oversize particles in the underflow of the vibratory separator.

In another aspect, embodiments disclosed herein relate to a method for measuring the operability of a vibratory separator. A portion of material is sampled from the underflow discharge line of a vibratory separator. The portion of material flows to a centrifugal sensing pump powered by an electric motor and then flows to a sampling screen. A baseline amount of power supplied to the electric motor is measured and recorded. The subsequent amount of power supplied to the electric motor is monitored and compared to the recorded baseline amount. The comparison of the subsequent amount of power supplied to the electric motor with the recorded baseline amount is used for measuring the operability of the vibratory separator.

Other aspects and advantages of the invention will be apparent from the following description and the appended claims.

DETAILED DESCRIPTION

Embodiments disclosed herein relate to an early warning system for detection of a failure condition in a vibratory separator. More specifically, embodiments disclosed herein relate to a system and method for detection of oversize particles in the underflow of a vibratory separator and a method for measuring the operability of a vibratory separator.

Generally, embodiments disclosed herein use a centrifugal pump to sense a failure condition of a vibratory separator, because a centrifugal pump uses less power when a flow of material through a screen is obstructed than it does for unimpeded flow. By pulling a small amount of the material off the underflow discharge line from a vibratory separator, redirecting the material through a small centrifugal sensing pump, and then redirecting the material through a sampling screen designed to pick up the oversize product, a drop in power to the centrifugal sensing pump resulting from an obstructed flow at the sampling screen may be electrically detected ("sensed") using a power supply measuring device. The power supply measuring device may be a wattmeter or a sensing relay, among other alternative devices. After detection, an alarm may be used to alert an operator of a failure condition of a component of the vibratory separator, or in alternative embodiments, a control switch may automatically shut down the vibratory separator.

Figure 1:
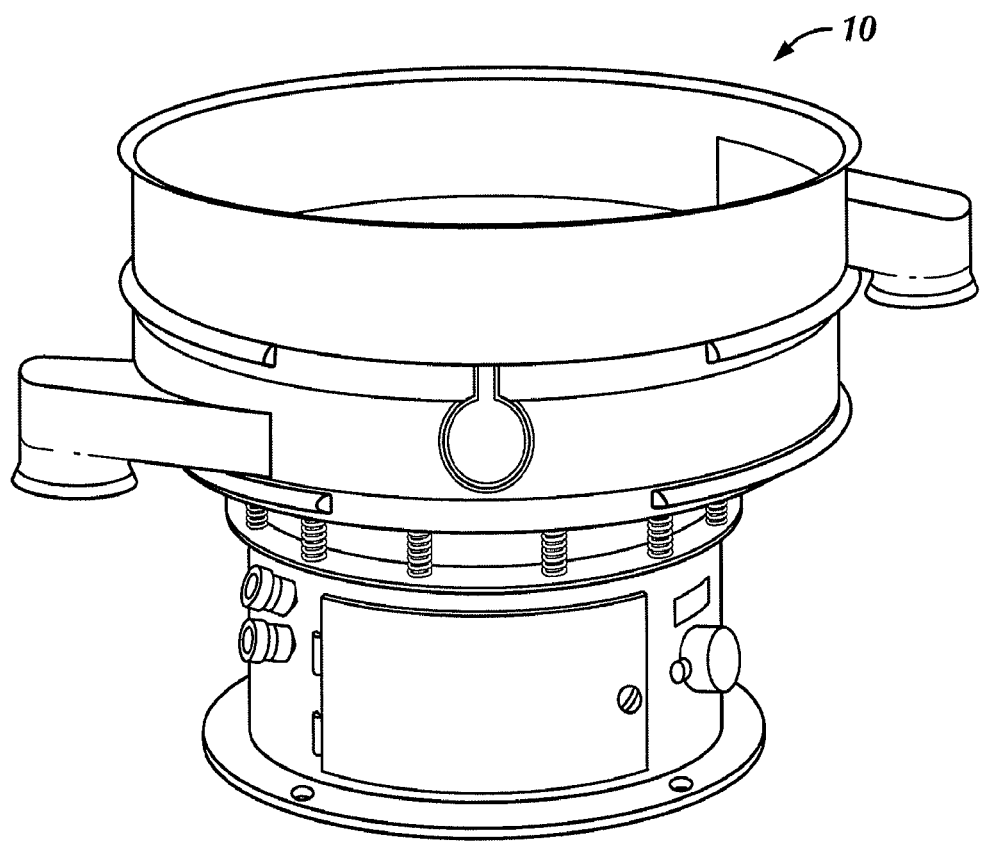
FIG. 1 shows a side view of a round vibratory separator according to one embodiment of the present disclosure.
Figure 2:
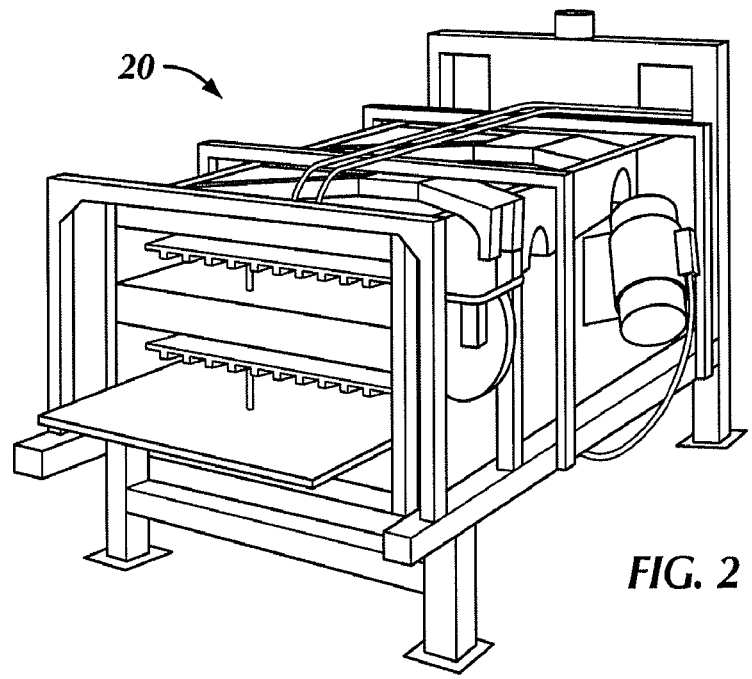
FIG. 2 shows an end view of a rectangular vibratory separator according to one embodiment of the present disclosure.

The disclosed subject matter may be used on round or rectangular vibratory separators, among others. Referring initially to FIG. 1, a side view of a round vibratory separator 10 according to one embodiment of the present disclosure is shown. Referring to FIG. 2, an end view of a rectangular vibratory separator 20 according to one embodiment of the present disclosure is shown. Those of ordinary skill in the art will appreciate that in alternative embodiments, the systems and methods disclosed herein may be used with any type vibratory separator known in the art.

In operation, a vibratory separator, such as the round separator 10 shown in FIG. 1 or the rectangular separator 20 shown in FIG. 2 may be actuated to provide a flow of materials through the vibratory separator, such that solid particles are divided according to relative size. As the materials flow over a screen, larger particles exit the vibratory separator through a discharge, while smaller particles exit through a secondary discharge area. The screen may include a plurality of filtering elements manufactured from metals, plastics, cloth, and/or composites. Screens may be selected based on mesh or micron size, among other sizing selection alternatives. Those of ordinary skill in the art will appreciate that in certain embodiments, multiple screens may be used, with each screen having a different screen size, thereby allowing for a plurality of discharges, each with a different allowable overs and unders percentage.

Figure 3B:
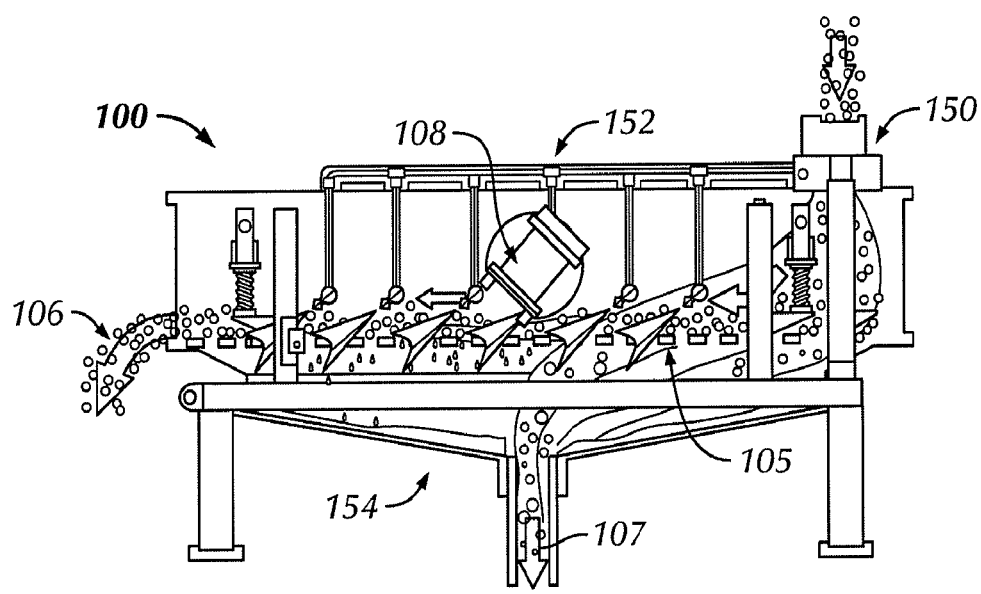
FIG. 3B shows a cut-away view of a rectangular vibratory separator according to one embodiment of the present disclosure.
Figure 3A:
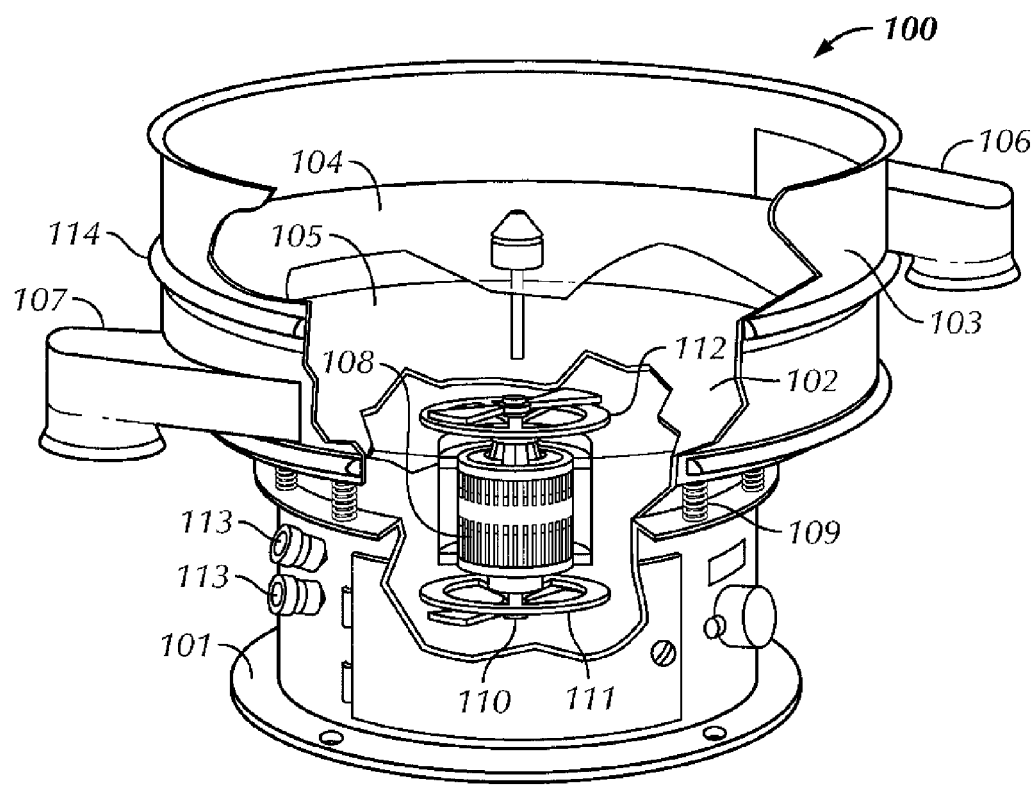
FIG. 3A shows a cut-away view of a round vibratory separator according to one embodiment of the present disclosure.

Referring to FIG. 3A, a cut-away view of an embodiment of a round vibratory separator 100 is shown. In this embodiment, vibratory separator 100 includes a base 101, a lower frame 102, an upper frame 103, and a screen 104. Vibratory separator 100 also includes a discharge area 105, an oversize discharge 106, and an undersize discharge 107. In this embodiment, the vibratory action of vibratory separator 100 is generated by a motion generator 108 disposed inside base 101. However, those of ordinary skill in the art will appreciate that in alternate embodiments, motion generator 108 may be disposed outside of base 101.

Vibratory separator 100 also includes springs 109 disposed between base 101 and lower frame 102 for restricting the motion of lower frame 102 and upper frame 103. In this embodiment, vibratory separator 100 has an angle adjuster 110, a lower force wheel 111, an upper force wheel 112, and a plurality of operation ports 113, that may be used to, for example, automate re-greasing of internal components. Those of ordinary skill in the art will appreciate that alternate embodiments may include a selected number of the above described components, or include additional components not specifically described, and still be within the scope of the present disclosure. For example, certain embodiments may include external quick-release clamps 114, a single discharge, a single frame, or multiple screens.

As noted above, the methods and systems disclosed herein may be used with rectangular vibratory separators. Referring to FIG. 3B, a cut-away view of an embodiment of a rectangular vibratory separator 100 is shown. In this embodiment, rectangular vibratory separator 100 uses a motion generator 108 to impart motion to materials passing therethrough. Vibratory separator 100 also includes a screen 105, an oversize discharge 106, and an undersize discharge 107. A flow of material enters via feed end 150 and passes stationary spray system 152. Screen 105 separates the material into oversize discharge 106 and undersize discharge 107, with undersize discharge (filtrate) entering sump pan 154.

In one embodiment, the methods and systems disclosed herein may be used with a vibratory separator 100 in a wet screening application. In such an application, a slurry may be supplied to vibratory separator 100. Generally, a slurry is a fluid with solids entrained therein. Common examples of slurries include mixtures of water and bentonite, wood pulp and water used to make paper, and drilling muds used in the oil field industry. In wet screening, separation of products based on particle size may be vitally important, and a failure to screen accordingly may lead to a large amount of final product being rejected or having to be reworked at a significant expense.

Figure 4:
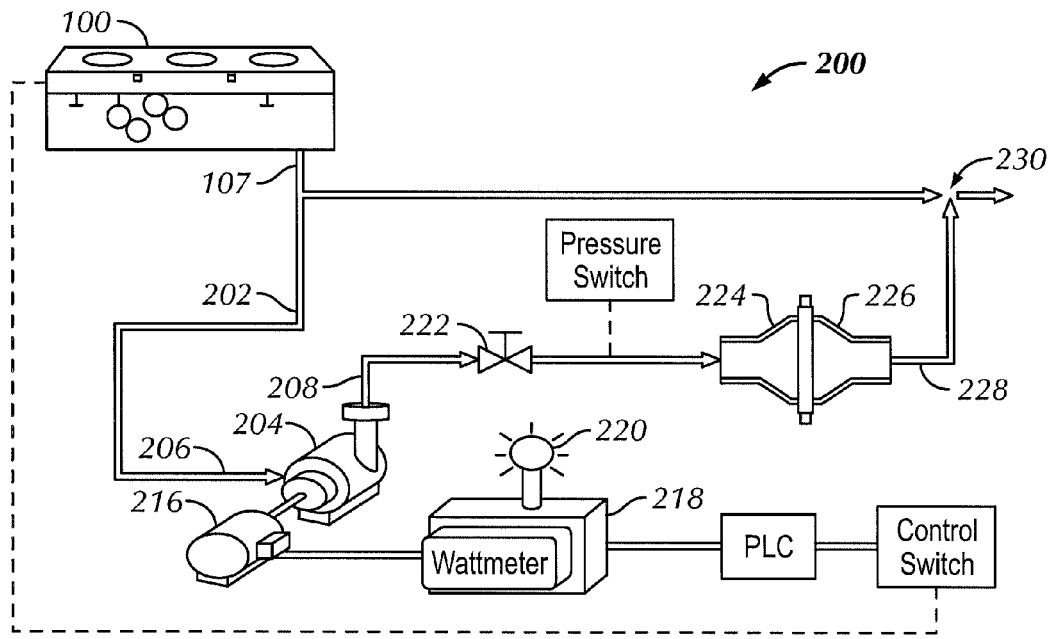
FIG. 4 shows a system for detecting oversize particles in the underflow of a vibratory separator according to one embodiment of the present disclosure.

Referring to FIG. 4, a schematic representation of a system 200 for detection of oversize particles in the underflow of a vibratory separator according to an embodiment of the present disclosure is shown. In this embodiment, sampling line 202 receives a portion of material from an underflow discharge line 107 of a vibratory separator 100. The received material includes a small amount of the finished product, which is redirected through a centrifugal sensing pump 204 having a centrifugal sensing pump input 206 and centrifugal sensing pump output 208. Sensing pump 204 is powered by an electric motor 216 and is operatively connected to a power supply measuring device 218. In one embodiment, power supply measuring device 218 is a wattmeter, while in an alternative embodiment, power supply measuring device 218 may include a sensing relay. In one embodiment, an alarm 220 is operatively connected to the power supply measuring device 218 and may be used for alerting an operator of a failure condition of a component of the vibratory separator. In other embodiments, a programmable logic controller (not shown) may be connected to vibratory separator 100 for actuation of an automated shut down procedure. In such an embodiment, the programmable logic controller (not shown) may determine, based on a power signal from power supply measuring device 218, that the vibratory separator 100 is not separating fluids at an acceptable level. Such determining functions will be discussed in detail below.

Downstream of centrifugal sensing pump output 208 is an optional calibration valve 222 (i.e., an adjustment valve), which may be used to restrict a flow rate of fluid from pump output 208, such that an optimal flow rate is achieved. Further downstream, a sampling screen 224 (also known as a "tattle screen") is in fluid communication with centrifugal sensing pump 204. In one embodiment, sampling screen 224 is housed in sampling screen housing 226. Fluid exits the sampling screen housing 226 via return line 228, which returns the sampled fluid to main underflow discharge line 107 at a connection point 230 downstream of initial sampling line 202.

In one embodiment, sampling screen 224 is mounted in sampling screen housing 226 using a quick clamp (not shown), so that screen 224 may be changed and/or cleaned. Screen 224 may have larger perforations than separator screen 104, so as to prevent false positives (e.g., if a 100 mesh screen is used for the separator screen 104, then a 50 mesh sampling screen 224 may be used). In one embodiment, a pressure switch (not shown) may be added between the pump output 208 and the sampling screen 224 as a redundant pressure check. A pressure switch is a type of switch that makes electrical contact when a certain set pressure has been reached on its input. Such switches may be used to provide on/off switching from a pneumatic source.

Figure 5:
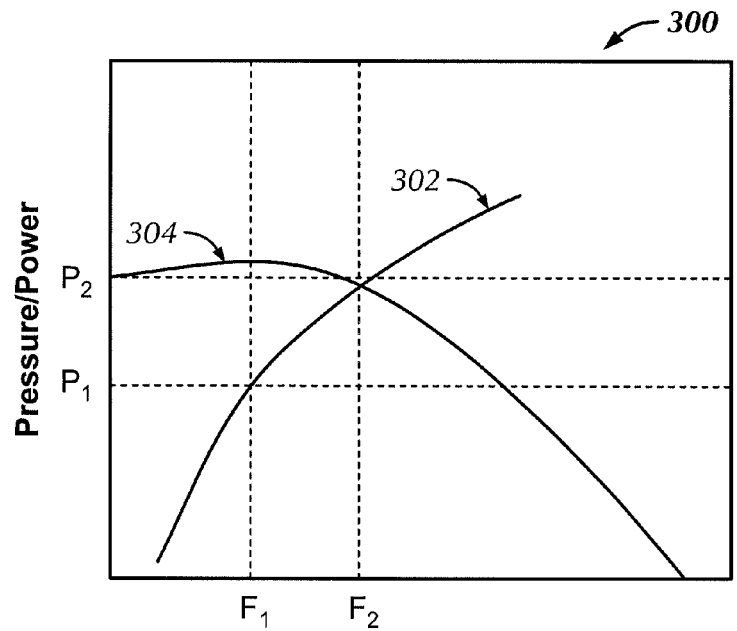
FIG. 5 shows a pressure versus power graph for a centrifugal sensing pump according to one embodiment of the present disclosure.

Referring to FIG. 5, a pressure versus power graph 300 according to an embodiment of the present disclosure is shown. The upward sloping line 302 represents a power curve of the pump, while the downward sloping line 304 represents a flow rate of the sample fluid. A reduction in power to the electric motor indicates an obstructed flow of material through the sampling screen as a result of oversize particles in the underflow discharge line of vibratory separator plugging perforations in the sampling screen. As the perforations in the sampling screen are plugged by oversize particles, the flow rate of the pump decreases. As such, the corresponding power required by the pump decreases, because centrifugal sensing pumps require less power when flow is obstructed than for an unimpeded flow. This reduction in power may be detected using a power supply measuring device. In one embodiment, this reduction in power may trigger an alarm at a predetermined set point. The alarm may be both aural and/or visual. In an alternative embodiment, a reduction in power may actuate an automated shut down procedure at a predetermined set point using a programmable logic controller. The programmable logic controller may be operatively connected to both the power supply measuring device and the vibratory separator, thereby allowing for automated shut down of the vibratory separator at a predetermined set point.

Figure 6:
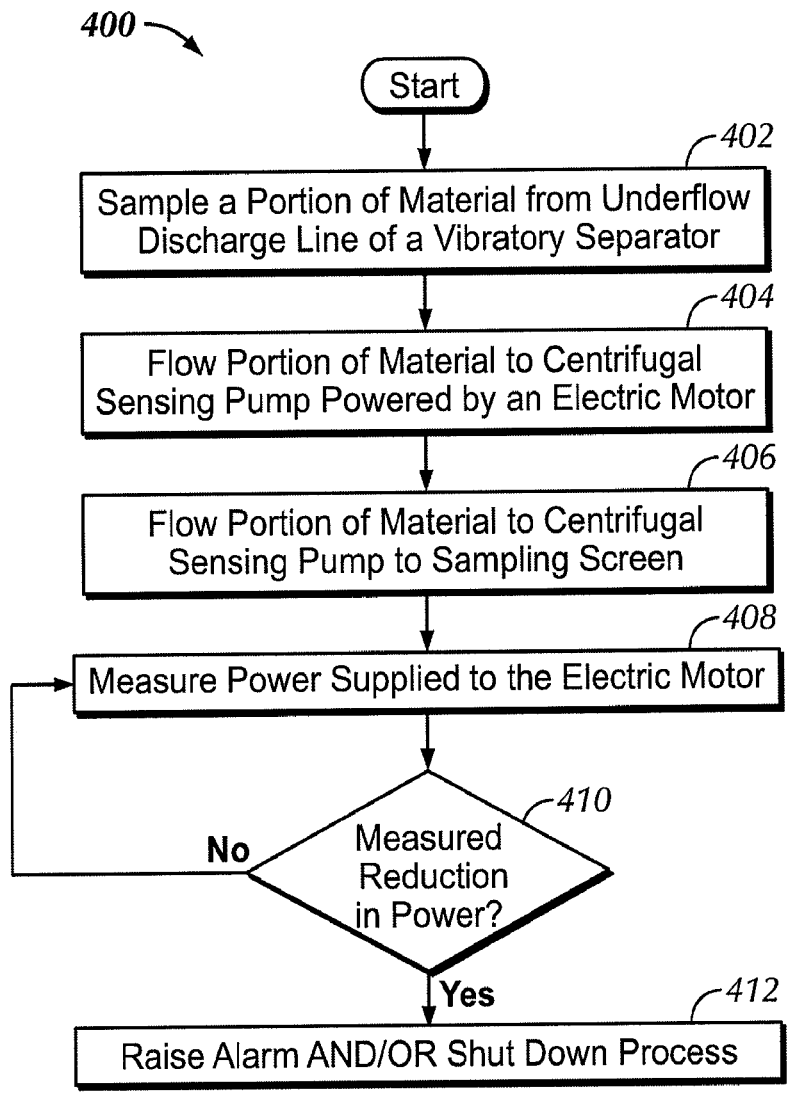
FIG. 6 shows a method for detecting oversize particles in the underflow of a vibratory separator according to one embodiment of the present disclosure.

Referring to FIG. 6, a method 400 for detection of oversize particles in the underflow of a vibratory separator is described. In step 402, a portion of material is sampled from an underflow discharge line of a vibratory separator. This is a small amount of the finished product, which is redirected through a centrifugal sensing pump in step 404. The centrifugal sensing pump is powered by an electric motor, with a power supply measuring device operatively connected thereto. In step 406, the discharge of the centrifugal sensing pump flows to a sampling screen. The sampling screen is designed to pick up oversize product, thereby obstructing the flow of the portion of material. Step 408 involves measuring the power supplied to the electric motor powering the centrifugal sensing pump. A reduction in power to the centrifugal sensing pump resulting from obstructed flow at the sampling screen may be electrically detected using a power supply measuring device. By measuring the reduction in power at 410, a reduction in flow of material through the sampling screen as a result of oversize particles in the underflow of the vibratory separator may be detected. Oversize particles in the underflow of the vibratory separator indicate that the vibratory separator is not separating fluids at an acceptable level. In optional step 412, an alarm may alert an operator of a failure condition of a component of the vibratory separator. Alternatively, a control switch may automatically shut down the vibratory separator process in step 412.

Figure 7:
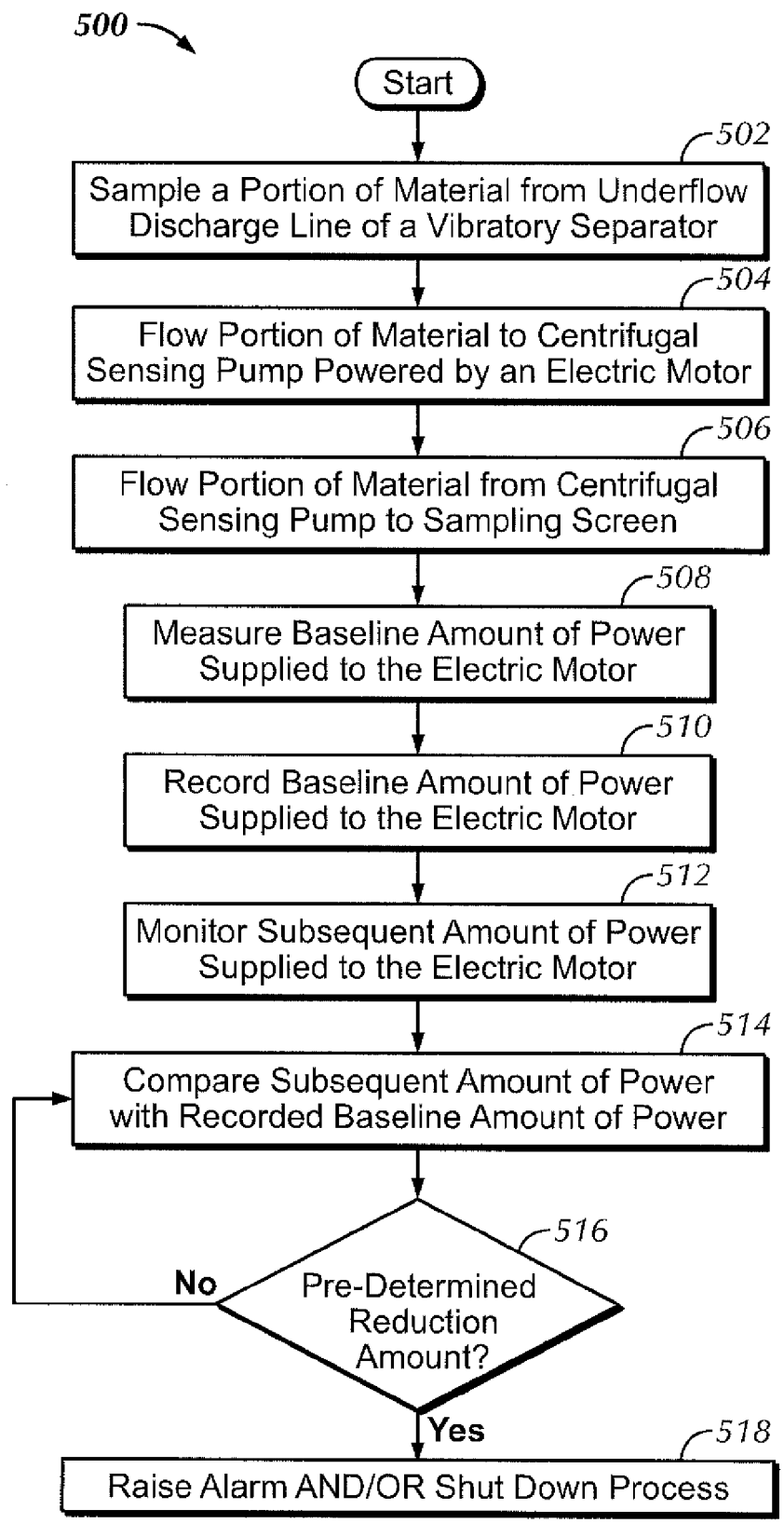
FIG. 7 shows a method for measuring the operability of a vibratory separator according to one embodiment of the present disclosure.

Referring to FIG. 7, a method 500 for measuring the operability of a vibratory separator is described. In step 502, a portion of material is sampled from an underflow discharge line of a vibratory separator. The portion of material is a small amount of the finished product, which is redirected through a small centrifugal sensing pump in step 504. The centrifugal sensing pump is powered by an electric motor, with a power supply measuring device operatively connected thereto. In step 506, the discharge of this centrifugal sensing pump flows to a sampling screen. The sampling screen is designed to pick up oversize product, thereby obstructing the flow of the portion of material. Step 508 involves measuring the baseline amount of power supplied to the electric motor powering the centrifugal sensing pump. This baseline amount of power is recorded in step 510. The subsequent amount of power supplied to the electric motor is monitored in step 512. The recorded baseline amount of power supplied to the electric motor is compared with the subsequent amount of power supplied to the electric motor in step 514. A predetermined reduction in the subsequent amount of power supplied to the electric motor compared to the recorded baseline amount of power supplied to the electric motor indicates a failure condition for the vibratory separator. The predetermined reduction may be a predetermined percentage reduction in amount of power supplied to the electric motor or a reduction in the absolute amount of power supplied to the electric motor. Step 516 indicates that if this predetermined reduction amount is reached, in step 518 an alarm may alert an operator of a reduction in flow of the portion of material. Alternatively, in step 518, an automated shut down procedure may be actuated. If the predetermined reduction amount is not reached, the method involves continuing to monitor the power supplied to the electric motor in step 512 and comparing this to the baseline amount of power in step 514.

As noted above, the predetermined reduction may be a predetermined percentage reduction in amount of power supplied to the electric motor or a reduction in the absolute amount of power supplied to the electric motor. In one embodiment, a percentage reduction between 5% and 15% compared to the baseline amount of power supplied to the electric motor may indicate an initial problem with the vibratory separator. In one embodiment, a percentage reduction of 10% may result in an alarm used for alerting an operator of the initial problem. In another embodiment, a percentage reduction between 15% and 35% may indicate a failure condition for the vibratory separator. In such an embodiment, a percentage reduction of 25% may result in an automated shut down procedure being actuated. Thus, in one embodiment a percentage reduction between 5% and 35% may indicate that there is a problem with the overall health of the vibratory separator. The overall health of the system may include the health of a screen, the separator, the way the screen is mounted, a gasket, and a failure of a pneumatic device associated with the gasket, among other health indicators. Those of ordinary skill in the art will appreciate that a predetermined absolute reduction in power may also be used.

Advantageously, embodiments of the present disclosure may be used in an industrial separation process, including clays and bentonite used in the paper milling industry, as well as for monitoring slurries and drilling muds used in the oilfield industry, among other alternative uses.

Also advantageously, embodiments of the present disclosure may be mounted remotely, or retroactively installed onto an existing separator, potentially resulting in cost savings.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed is:

1. A system comprising:
   a sampling line, in fluid connection with an underflow discharge line of a vibratory separator, wherein the sampling line is configured to receive a portion of material from the underflow discharge line;
   a sensing pump comprising:
      a sensing pump input in fluid connection with the sampling line; and
      a sensing pump output;
   a sampling screen in fluid connection with the sensing pump output;
   a return line in fluid connection with the sampling screen, wherein the return line is configured to return the portion of material to the underflow discharge line downstream of the sampling line;
   an electric motor for powering the sensing pump; and
   a power supply measuring device operatively connected to the electric motor and configured to measure a supply of power to the sensing pump.

2. The system of claim 1, further comprising an alarm operatively connected to the power supply measuring device.

3. The system of claim 2, wherein the alarm comprises an aural alarm.

4. The system of claim 2, wherein the alarm comprises a visual alarm.

5. The system of claim 1, further comprising a programmable logic controller operatively connected to the power supply measuring device.

6. The system of claim 5, further comprising a control switch operatively connected to the programmable logic controller.

7. The system of claim 1, wherein the power supply measuring device comprises a wattmeter.

8. The system of claim 1, wherein the power supply measuring device comprises a sensing relay.

9. The system of claim 1, further comprising a sampling screen housing configured to hold the sampling screen.

10. The system of claim 1, further comprising a calibration valve downstream of the sensing pump output.

11. The system of claim 1, further comprising a pressure switch downstream of the sensing pump output.

12. The system of claim 1, wherein the sensing pump is a centrifugal pump.

13. A method comprising:
   sampling a portion of material from an underflow discharge line of a vibratory separator;
   flowing the portion of material to a centrifugal sensing pump;
   flowing the portion of material from the centrifugal sensing pump to a sampling screen; and
   measuring power supplied to an electric motor for powering the centrifugal sensing pump.

14. The method of claim 13, further comprising raising an alarm at a predetermined set point, the predetermined set point based on a predetermined reduction in power supplied to the centrifugal sensing pump.

15. The method of claim 13, further comprising actuating an automated vibratory separator shut down procedure at a predetermined set point, the predetermined set point based on a predetermined reduction in power supplied to the centrifugal sensing pump.

16. A method comprising:
   sampling a portion of material from a vibratory separator;
   flowing the portion of material to a centrifugal sensing pump;
   flowing the portion of material from the centrifugal sensing pump to a sampling screen;
   measuring a baseline amount of power supplied to the centrifugal pump;
   monitoring a subsequent amount of power supplied to the centrifugal pump; and
   comparing the subsequent amount of power supplied to the centrifugal pump to the baseline amount of power supplied to the centrifugal pump.

17. The method of claim 16, further comprising raising an alarm based on a predetermined reduction in the subsequent amount of power supplied to the centrifugal pump.

18. The method of claim 17, wherein the step of raising an alarm based on a predetermined reduction comprises raising an alarm based on a reduction of between 5% and 15% in the subsequent amount of power supplied to the centrifugal pump compared to the baseline amount of power supplied to the centrifugal pump.

19. The method of claim 17, wherein the step of raising an alarm based on a predetermined reduction comprises raising an alarm based on a reduction of 10% in the subsequent amount of power supplied to the centrifugal pump compared to the baseline amount of power supplied to the centrifugal pump.

20. The method of claim 16, further comprising actuating an automated vibratory separator shut down procedure based on a predetermined reduction in the subsequent amount of power supplied to the centrifugal pump compared to the baseline amount of power supplied to the centrifugal pump.

* * * * *